(12) United States Patent
Duncan et al.

(10) Patent No.: US 8,865,626 B2
(45) Date of Patent: Oct. 21, 2014

(54) SYNERGISTICALLY ACTIVE HERBICIDAL AGENTS THAT ARE COMPATIBLE WITH CULTIVATED PLANTS AND CONTAIN HERBICIDES FROM THE GROUP OF BENZOYLPYRAZOLES

(75) Inventors: Nick Duncan, Sudbury (GB); Allan Eadie, Düsseldorf (DE)

(73) Assignee: Bayer Cropscience AG, Monheim (DE)

( * ) Notice: Subject to any disclaimer, the term of this patent is extended or adjusted under 35 U.S.C. 154(b) by 1030 days.

(21) Appl. No.: 12/515,778

(22) PCT Filed: Nov. 16, 2007

(86) PCT No.: PCT/EP2007/009920
§ 371 (c)(1),
(2), (4) Date: Dec. 29, 2009

(87) PCT Pub. No.: WO2008/064781
PCT Pub. Date: Jun. 5, 2008

(65) Prior Publication Data
US 2010/0144523 A1    Jun. 10, 2010

(30) Foreign Application Priority Data
Nov. 28, 2006    (DE) .......................... 10 2006 056 083

(51) Int. Cl.
| | | |
|---|---|---|
| A01N 43/56 | (2006.01) | |
| A01N 25/32 | (2006.01) | |
| A01N 43/40 | (2006.01) | |
| A01N 43/60 | (2006.01) | |
| A01N 43/90 | (2006.01) | |
| A01N 47/36 | (2006.01) | |

(52) U.S. Cl.
CPC ............... *A01N 43/56* (2013.01); *A01N 47/36* (2013.01)
USPC ........... 504/280; 504/105; 504/107; 504/108; 504/130; 504/136; 504/139; 504/212; 504/214; 504/241

(58) Field of Classification Search
USPC ......... 504/129, 105, 107, 108, 130, 136, 139, 504/212, 214, 241, 280
See application file for complete search history.

(56) References Cited

U.S. PATENT DOCUMENTS

| | | | |
|---|---|---|---|
| 2002/0065200 A1 * | 5/2002 | Schmitt et al. | ................ 504/282 |
| 2003/0158039 A1 | 8/2003 | Schmitt et al. | |
| 2006/0234862 A1 * | 10/2006 | Huff et al. | ..................... 504/111 |
| 2008/0004180 A1 | 1/2008 | Dollinger et al. | |

FOREIGN PATENT DOCUMENTS

| | | | |
|---|---|---|---|
| CA | 2467976 A1 * | 5/2003 | |
| EP | 1652132 A3 | 7/2006 | |
| WO | 03/043422 A1 | 5/2003 | |
| WO | 2006/024411 A2 | 3/2006 | |
| WO | 2006/103002 A1 | 10/2006 | |

OTHER PUBLICATIONS

International Search Report for PCT/EP07/09920, mailed May 8, 2008.

* cited by examiner

*Primary Examiner* — Johann R Richter
*Assistant Examiner* — Andriae M Holt
(74) *Attorney, Agent, or Firm* — Miles and Stockbridge

(57) ABSTRACT

Synergistic and crop-plant-compatible herbicidal compositions comprising herbicides from the group of the benzoylpyrazoles
Herbicidal compositions comprising
A) a compound from the group of the benzoylpyrazoles,
B) at least one further herbicide and
C) optionally at least one safener
are described as herbicides effective against monocotyledonous and/or dicotyledonous harmful plants.
Compared to the herbicides applied individually, these compositions have superior activity, and at the same time they are highly compatible with crop plants.

22 Claims, No Drawings

SYNERGISTICALLY ACTIVE HERBICIDAL AGENTS THAT ARE COMPATIBLE WITH CULTIVATED PLANTS AND CONTAIN HERBICIDES FROM THE GROUP OF BENZOYLPYRAZOLES

CROSS REFERENCE TO RELATED APPLICATIONS

This application is a §371 National Stage Application of PCT/EP07/09920, filed Nov. 28, 2007, which claims priority to German Application 10 2006 056083.3, filed Nov. 28, 2006.

BACKGROUND OF THE INVENTION

1. Field of the Invention

The invention relates to the technical field of crop protection compositions which can be used against unwanted vegetation and which comprise, as active compounds, a combination of at least two herbicides and optionally one safener.

2. Description of Related Art

More specifically, it relates to herbicidal compositions comprising, as active compound, the herbicide pyrasulfotole in combination with at least one further herbicide and optionally one safener.

From WO 03/043422, it is known that herbicidal compositions comprising pyrasulfotole in combination with certain herbicides have synergistic properties. From WO 03/043423, it is known that herbicidal compositions comprising pyrasulfotole and certain safeners have crop-plant-compatible properties. From WO 2006/103002, it is known that herbicidal compositions comprising pyrasulfotole, certain herbicides and certain safeners have synergistic crop-plant-compatible properties.

However, in practice, i.e. in particular in the control of unwanted plants in the cultivation of cereals, the herbicidal compositions disclosed in these publications do not always meet the demands made on modern herbicides. Thus, depending on the site, the spectrum of unwanted plants that can be controlled is not always sufficient, or the safener action in the herbicidal composition is insufficient.

SUMMARY OF THE INVENTION

It is an object of the present invention to provide herbicidal compositions having properties which are improved compared to the prior art.

The invention provides selected herbicidal compositions comprising an effective amount of
A) the herbicide pyrasulfotole of the formula (A) or an agriculturally customary salt thereof (component (A)),

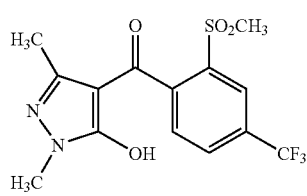
(A)

B) at least one herbicide (component (B)) from the group comprising aminopyralid, carfentrazone-ethyl, imazamoxammonium and pyroxsulam, where these compositions comprise the components (A) and (B) in a weight ratio of from 1:200 to 200:1, preferably from 1:100 to 100:1, particularly preferably from 1:50 to 50:1.

DETAILED DESCRIPTION OF A PREFERRED EMBODIMENT

The invention furthermore provides selected herbicidal compositions comprising an effective amount of
A) the herbicide pyrasulfotole of the formula (A) or an agriculturally customary salt thereof (component (A)),

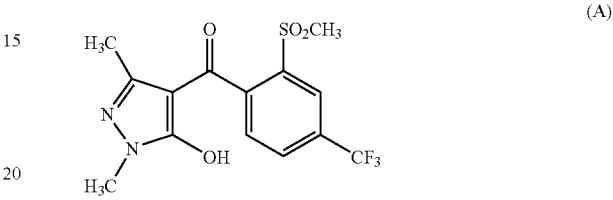
(A)

B) at least one herbicide (component (B)) from the group comprising aminopyralid, carfentrazone-ethyl, flucarbazone-sodium, florasulam, imazamoxammonium, iodosulfuron-methyl-sodium, mesosulfuron-methyl, sethoxydim and pyroxsulam, and C) an amount, acting as an antidote, of at least one safener (component (C)) from the group comprising mefenpyr-diethyl, cloquintocet-mexyl and isoxadifen-ethyl, where these compositions comprise the components (A), (B) and (C) in a weight ratio of x:y:z, where x, y and z in each case independently of one another may assume values of from 1 to 200, preferably from 1 to 100, particularly preferably from 1 to 50.

Hereinbelow, the terms "component (A)" and "herbicide (A)" are to be understood as having the same meaning. This applies analogously to the terms "component (B)" and "herbicide (B)" and also "component (C)" and "safener (C)".

The herbicide pyrasulfotole is known, for example, from WO 01/74785 and from the website "http://www.alanwood.net/pesticides/index.html". The chemical structures of the other active compounds, referred to above by their common names, are known, for example, from "The Pesticide Manual" 14th edition, 2006, British Crop Protection Council, and from the website "http://www.alanwood.net/pesticides/index.html" bekannt. If, in the context of this description, the short form of the common name of an active compound is used, this includes in each case all customary derivatives, such as esters and salts, and isomers, in particular optical isomers, and in particular the commercially available form or forms. If the common name refers to an ester or salt, it also includes in each case all other customary derivatives, such as other esters and salts, the free acids and neutral compounds, and isomers, in particular optical isomers, in particular the commercially available form or forms. The stated chemical compound names refer to at least one of the compounds embraced by the common name, frequently a preferred compound. In a preferred embodiment, the herbicidal compositions according to the invention are synergistically active and at the same time highly compatible with crop plants. The synergistic actions and the high compatibility with crop plants can be observed, for example, when components (A), (B) and (C) are applied together, and frequently they can also be observed when the components are applied at different times (splitting). It is also possible to apply the individual herbicides and safeners or the herbicide/safener combinations in a plurality of portions (sequential application), for example applications by the pre-emergence method, followed by post-emergence applications or early post-emergence applications, followed by applications at medium or late post-emergence. Preferred is the joint or nearly simultaneous application of the active compounds of the herbicide combination according to the invention.

The synergistic effects permit a reduction of the application rates of the individual active compounds, a higher efficacy at the same application rate, the control of species which are as yet uncontrolled (gaps), an extension of the period of application and/or a reduction in the number of individual applications required and—as a result for the user—weed control systems which are more advantageous economically and ecologically.

The invention also embraces herbicidal compositions comprising, in addition to components (A), (B) and (C) one or more further agrochemically active compound(s) of a different structure, such as herbicides, insecticides, fungicides or safeners. The preferred conditions illustrated above and below also apply to these herbicidal compositions.

The invention likewise also embraces herbicidal compositions comprising, in addition to components (A), (B) and (C), fertilizers, such as ammonium sulfate, ammonium nitrate, urea, potassium nitrate and mixtures thereof. The preferred conditions illustrated above and below also apply to these herbicidal compositions.

The invention furthermore embraces herbicidal compositions comprising, in addition to components (A), (B) and (C), adjuvants, such as emulsifiers, dispersants, mineral and vegetable oils and mixtures thereof. The preferred conditions illustrated above and below also apply to these herbicidal compositions.

Of particular interest are herbicidal compositions comprising one or more of the following combinations of two compounds (A+B):

pyrasulfotole+aminopyralid-tris(2-hydroxypropyl)ammonium,
pyrasulfotole+carfentrazone-ethyl, pyrasulfotole+pyroxsulam,
pyrasulfotole+imazamox-ammonium.

Of particular interest are also herbicidal compositions comprising one or more of the following combinations of three compounds (A+B+C):

pyrasulfotole+aminopyralid+mefenpyr-diethyl,
pyrasulfotole+aminopyralid+cloquintocet-mexyl,
pyrasulfotole+aminopyralid+isoxadifen-ethyl,
pyrasulfotole+carfentrazone-ethyl+mefenpyr-diethyl,
pyrasulfotole+carfentrazone-ethyl+cloquintocet-mexyl,
pyrasulfotole+carfentrazone-ethyl+isoxadifen-ethyl,
pyrasulfotole+flucarbazone-sodium+mefenpyr-diethyl,
pyrasulfotole+flucarbazone-sodium+cloquintocet-mexyl,
pyrasulfotole+flucarbazone-sodium+isoxadifen-ethyl,
pyrasulfotole+florasulam+mefenpyr-diethyl,
pyrasulfotole+florasulam+cloquintocet-mexyl,
pyrasulfotole+florasulam+isoxadifen-ethyl,
pyrasulfotole+imazamox-ammonium+mefenpyr-diethyl,
pyrasulfotole+imazamox-ammonium+cloquintocet-mexyl,
pyrasulfotole+imazamox-ammonium+isoxadifen-ethyl,
pyrasulfotole+iodosulfuron-methyl-sodium+mefenpyr-diethyl,
pyrasulfotole+iodosulfuron-methyl-sodium+cloquintocet-mexyl,
pyrasulfotole+iodosulfuron-methyl-sodium+isoxadifen-ethyl,
pyrasulfotole+mesosulfuron-methyl+mefenpyr-diethyl,
pyrasulfotole+mesosulfuron-methyl+cloquintocet-mexyl,
pyrasulfotole+mesosulfuron-methyl+isoxadifen-ethyl,
pyrasulfotole+sethoxydim+mefenpyr-diethyl,
pyrasulfotole+sethoxydim+cloquintocet-mexyl,
pyrasulfotole+sethoxydim+isoxadifen-ethyl,
pyrasulfotole+pyroxsulam+mefenpyr-diethyl,
pyrasulfotole+pyroxsulam+cloquintocet-mexyl,
pyrasulfotole+pyroxsulam+isoxadifen-ethyl.

In a further preferred embodiment, the herbicidal compositions according to the invention comprise the herbicide (A), two different components (B) and a safener (C):

pyrasulfotole+aminopyralid+carfentrazone-ethyl+mefenpyr-diethyl,
pyrasulfotole+aminopyralid+carfentrazone-ethyl+cloquintocet-mexyl,
pyrasulfotole+aminopyralid+carfentrazone-ethyl+isoxadifen-ethyl,
pyrasulfotole+aminopyralid+flucarbazone-sodium+mefenpyr-diethyl,
pyrasulfotole+aminopyralid+flucarbazone-sodium+cloquintocet-mexyl,
pyrasulfotole+aminopyralid+flucarbazone-sodium+isoxadifen-ethyl,
pyrasulfotole+aminopyralid+florasulam+mefenpyr-diethyl,
pyrasulfotole+aminopyralid+florasulam+cloquintocet-mexyl,
pyrasulfotole+aminopyralid+florasulam+isoxadifen-ethyl,
pyrasulfotole+aminopyralid+imazamox-ammonium+mefenpyr-diethyl,
pyrasulfotole+aminopyralid+imazamox-ammonium+cloquintocet-mexyl,
pyrasulfotole+aminopyralid+imazamox-ammonium+isoxadifen-ethyl,
pyrasulfotole+aminopyralid+pyrasulfotole+iodosulfuron+mefenpyr-diethyl,
pyrasulfotole+aminopyralid+pyrasulfotole+iodosulfuron-methyl-sodium+cloquintocet-mexyl,
pyrasulfotole+aminopyralid+pyrasulfotole+iodosulfuron-methyl-sodium+isoxadifen-ethyl,
pyrasulfotole+aminopyralid+mesosulfuron-methyl+mefenpyr-diethyl,
pyrasulfotole+aminopyralid+mesosulfuron-methyl+cloquintocet-mexyl,
pyrasulfotole+aminopyralid+mesosulfuron-methyl+isoxadifen-ethyl,
pyrasulfotole+aminopyralid+sethoxydim+mefenpyr-diethyl,
pyrasulfotole+aminopyralid+sethoxydim+cloquintocet-mexyl,
pyrasulfotole+aminopyralid+sethoxydim+isoxadifen-ethyl,
pyrasulfotole+aminopyralid+pyroxsulam+mefenpyr-diethyl,
pyrasulfotole+aminopyralid+pyroxsulam+cloquintocet-mexyl,
pyrasulfotole+aminopyralid+pyroxsulam+isoxadifen-ethyl,
pyrasulfotole+carfentrazone-ethyl+flucarbazone-sodium+mefenpyr-diethyl,
pyrasulfotole+carfentrazone-ethyl+flucarbazone-sodium+cloquintocet-mexyl,
pyrasulfotole+carfentrazone-ethyl+flucarbazone-sodium+isoxadifen-ethyl,
pyrasulfotole+carfentrazone-ethyl+florasulam+mefenpyr-diethyl, pyrasulfotole+carfentrazone-ethyl+florasulam+cloquintocet-mexyl,
pyrasulfotole+carfentrazone-ethyl+florasulam+isoxadifen-ethyl,
pyrasulfotole+carfentrazone-ethyl+imazamox-ammonium+mefenpyr-diethyl,
pyrasulfotole+carfentrazone-ethyl+imazamox-ammonium+cloquintocet-mexyl,
pyrasulfotole+carfentrazone-ethyl+imazamox-ammonium+isoxadifen-ethyl,
pyrasulfotole+carfentrazone-ethyl+iodosulfuron-methyl-sodium+mefenpyr-diethyl,
pyrasulfotole+carfentrazone-ethyl+iodosulfuron-methyl-sodium+cloquintocet-mexyl,
pyrasulfotole+carfentrazone-ethyl+iodosulfuron-methyl-sodium+isoxadifen-ethyl,
pyrasulfotole+carfentrazone-ethyl+mesosulfuron-methyl+mefenpyr-diethyl,
pyrasulfotole+carfentrazone-ethyl+mesosulfuron-methyl+cloquintocet-mexyl,
pyrasulfotole+carfentrazone-ethyl+mesosulfuron-methyl+isoxadifen-ethyl,
pyrasulfotole+carfentrazone-ethyl+sethoxydim+mefenpyr-diethyl,
pyrasulfotole+carfentrazone-ethyl+sethoxydim+cloquintocet-mexyl,
pyrasulfotole+carfentrazone-ethyl+sethoxydim+isoxadifen-ethyl,
pyrasulfotole+carfentrazone-ethyl+pyroxsulam+mefenpyr-diethyl,
pyrasulfotole+carfentrazone-ethyl+pyroxsulam+cloquintocet-mexyl,
pyrasulfotole+carfentrazone-ethyl+pyroxsulam+isoxadifen-ethyl,
pyrasulfotole+flucarbazone-sodium+florasulam+mefenpyr-diethyl,
pyrasulfotole+flucarbazone-sodium+florasulam+cloquintocet-mexyl,
pyrasulfotole+flucarbazone-sodium+florasulam+isoxadifen-ethyl,
pyrasulfotole+flucarbazone-sodium+imazamox-ammonium+mefenpyr-diethyl,
pyrasulfotole+flucarbazone-sodium+imazamox-ammonium+cloquintocet-mexyl,
pyrasulfotole+flucarbazone-sodium+imazamox-ammonium+isoxadifen-ethyl,
pyrasulfotole+flucarbazone-sodium+iodosulfuron-methyl-sodium+mefenpyr-diethyl,
pyrasulfotole+flucarbazone-sodium+iodosulfuron-methyl-sodium+cloquintocet-mexyl,
pyrasulfotole+flucarbazone-sodium+iodosulfuron-methyl-sodium+isoxadifen-ethyl,
pyrasulfotole+flucarbazone-sodium+mesosulfuron-methyl+mefenpyr-diethyl,
pyrasulfotole+flucarbazone-sodium+mesosulfuron-methyl+cloquintocet-mexyl,
pyrasulfotole+flucarbazone-sodium+mesosulfuron-methyl+isoxadifen-ethyl,
pyrasulfotole+flucarbazone-sodium+sethoxydim+mefenpyr-diethyl,
pyrasulfotole+flucarbazone-sodium+sethoxydim+cloquintocet-mexyl,
pyrasulfotole+flucarbazone-sodium+sethoxydim+isoxadifen-ethyl,
pyrasulfotole+flucarbazone-sodium+pyroxsulam+mefenpyr-diethyl,
pyrasulfotole+flucarbazone-sodium+pyroxsulam+cloquintocet-mexyl,
pyrasulfotole+flucarbazone-sodium+pyroxsulam+isoxadifen-ethyl,
pyrasulfotole+florasulam+imazamox-ammonium+mefenpyr-diethyl,
pyrasulfotole+florasulam+imazamox-ammonium+cloquintocet-mexyl,
pyrasulfotole+florasulam+imazamox-ammonium+isoxadifen-ethyl,
pyrasulfotole+florasulam+iodosulfuron-methyl-sodium+mefenpyr-diethyl,
pyrasulfotole+florasulam+iodosulfuron-methyl-sodium+cloquintocet-mexyl,
pyrasulfotole+florasulam+iodosulfuron-methyl-sodium+isoxadifen-ethyl,
pyrasulfotole+florasulam+mesosulfuron-methyl+mefenpyr-diethyl,
pyrasulfotole+florasulam+mesosulfuron-methyl+cloquintocet-mexyl,
pyrasulfotole+florasulam+mesosulfuron-methyl+isoxadifen-ethyl,
pyrasulfotole+florasulam+sethoxydim+mefenpyr-diethyl,
pyrasulfotole+florasulam+sethoxydim+cloquintocet-mexyl,
pyrasulfotole+florasulam+sethoxydim+isoxadifen-ethyl,
pyrasulfotole+florasulam+pyroxsulam+mefenpyr-diethyl,
pyrasulfotole+florasulam+pyroxsulam+cloquintocet-mexyl,
pyrasulfotole+florasulam+pyroxsulam+isoxadifen-ethyl,
pyrasulfotole+imazamox-ammonium+iodosulfuron-methyl-sodium+mefenpyr-diethyl,
pyrasulfotole+imazamox-ammonium+iodosulfuron-methyl-sodium+cloquintocet-mexyl,
pyrasulfotole+imazamox-ammonium+iodosulfuron-methyl-sodium+isoxadifen-ethyl,
pyrasulfotole+imazamox-ammonium+mesosulfuron-methyl+mefenpyr-diethyl,
pyrasulfotole+imazamox-ammonium+mesosulfuron-methyl+cloquintocet-mexyl,
pyrasulfotole+imazamox-ammonium+mesosulfuron-methyl+isoxadifen-ethyl,
pyrasulfotole+imazamox-ammonium+sethoxydim+mefenpyr-diethyl,
pyrasulfotole+imazamox-ammonium+sethoxydim+cloquintocet-mexyl,
pyrasulfotole+imazamox-ammonium+sethoxydim+isoxadifen-ethyl,
pyrasulfotole+imazamox-ammonium+pyroxsulam+mefenpyr-diethyl,
pyrasulfotole+imazamox-ammonium+pyroxsulam+cloquintocet-mexyl,
pyrasulfotole+imazamox-ammonium+pyroxsulam+isoxadifen-ethyl,
pyrasulfotole+iodosulfuron-methyl-sodium+mesosulfuron-methyl+mefenpyr-diethyl,
pyrasulfotole+iodosulfuron-methyl-sodium+mesosulfuron-methyl+cloquintocet-mexyl,
pyrasulfotole+iodosulfuron-methyl-sodium+mesosulfuron-methyl+isoxadifen-ethyl,
pyrasulfotole+iodosulfuron-methyl-sodium+sethoxydim+mefenpyr-diethyl,
pyrasulfotole+iodosulfuron-methyl-sodium+sethoxydim+cloquintocet-mexyl,
pyrasulfotole+iodosulfuron-methyl-sodium+sethoxydim+isoxadifen-ethyl, pyrasulfotole+iodosulfuron-methyl-sodium+pyroxsulam+mefenpyr-diethyl,
pyrasulfotole+iodosulfuron-methyl-sodium+pyroxsulam+cloquintocet-mexyl,
pyrasulfotole+iodosulfuron-methyl-sodium+pyroxsulam+isoxadifen-ethyl,
pyrasulfotole+mesosulfuron-methyl+sethoxydim+mefenpyr-diethyl,
pyrasulfotole+mesosulfuron-methyl+sethoxydim+cloquintocet-mexyl,
pyrasulfotole+mesosulfuron-methyl+sethoxydim+isoxadifen-ethyl,
pyrasulfotole+mesosulfuron-methyl+pyroxsulam+mefenpyr-diethyl,
pyrasulfotole+mesosulfuron-methyl+pyroxsulam+cloquintocet-mexyl,
pyrasulfotole+mesosulfuron-methyl+pyroxsulam+isoxadifen-ethyl,
pyrasulfotole+sethoxydim+pyroxsulam+mefenpyr-diethyl,
pyrasulfotole+sethoxydim+pyroxsulam+cloquintocet-mexyl,
pyrasulfotole+sethoxydim+pyroxsulam+isoxadifen-ethyl.

For the herbicidal compositions according to the invention, the application rates required are generally in the range from 1 to 2000 g, preferably from 10 to 1000 g, particularly preferably from 10 to 300 g of active substance per hectare (ai/ha) of component (A) and from 1 to 2000 g, preferably from 1 to 1000 g, particularly preferably from 5 to 500 g, of component (B) and from 1 to 1000 g, preferably from 1 to 500 g, particularly preferably from 5 to 250 g of component (C).

The weight ratios of the components (A) to (B) on the one hand and (A+B) to (C) on the other hand can be varied within wide ranges. The ratio of the components (A) to (B) is preferably in the range from 1:100 to 100:1, particularly preferably in the range from 1:50 to 50:1, especially in the range from 1:20 to 20:1. The ratio of the components (A+B) to (C) is preferably in the range from 1:10 to 50:1, in particular in the range from 1:5 to 20:1. The ranges mentioned above also apply to the case where the herbicidal compositions according to the invention comprise more than one component (B) and/or component (C). In this case, the numbers mentioned apply to the sum of the individual values of the components (B) or (C).

Optimum weight ratios may depend on the particular field of application, on the weed spectrum and on the active compound combination used and can be determined in preliminary experiments.

The compositions according to the invention can be employed for the selective control of annual and perennial monocotyledonous and dicotyledonous harmful plants in crops of cereals (for example barley, oats, rye, wheat), corn and rice and in crops of transgenic useful plants or crops of useful plants selected by classical means which are resistant to the active compounds (A) and (B). Likewise, they can be employed for controlling unwanted harmful plants in plantation crops such as oil palm, coconut palm, indian-rubber tree, citrus, pineapple, cotton, coffee, cocoa and the like, and also in fruit production and viticulture. By virtue of their good compatibility, they are particularly suitable for use in cereals and corn, especially cereals.

The compositions according to the invention act against a broad spectrum of weeds. They are suitable for controlling annual and perennial harmful plants such as, for example, from the species *Abutilon, Alopecurus, Avena, Chenopodium, Cynoden, Cyperus, Digitaria, Echinochloa, Elymus, Galium, Ipomoea, Kochia, Lamium, Matricaria, Polygonum, Scirpus, Setaria, Sorghum, Veronica, Viola* and *Xanthium*.

A further advantage of the compositions according to the invention is their excellent action against many harmful plants which have now become resistant to sulfonylureas, such as, for example, *Kochia*.

The invention also provides a method for controlling unwanted vegetation, which comprises applying the herbicide (A) and one or more herbicides (B) and one or more safeners (C) to the harmful plants, to parts of the harmful plants or to the area under cultivation.

The herbicidal compositions according to the invention are also distinguished by the fact that the effective dosages of the components (A) and (B) used in the combinations are reduced with respect to an individual dosage, so that it is possible to reduce the required active compound application rates (synergistic effect). At the same time, the compatibility with crop plants is more pronounced by the presence of the safener (C) than in the case of a combination of the safener (C) with the herbicide (A) or a herbicide (B). The synergistic effects permit the application rate to be reduced, a broader spectrum of broad-leaved weeds and weed grasses to be controlled, a more rapid onset of the herbicidal action, a longer persistency, better control of the harmful plants by only one application, or few applications, and widening of the period of time within which the product can be used. These properties are required in weed control practice to keep agricultural crops free from unwanted competing plants and thus to ensure and/or to increase quality and quantity of the yields. These novel combinations markedly surpass the prior art with respect to the described properties.

The herbicidal compositions according to the invention can be applied both as mixed formulations of the herbicides (A) and (B) and the safener (C), if appropriate together with other customary formulation auxiliaries, which mixed formulations are then applied in the usual manner in the form of a dilution with water, or else they can be prepared in the form of tank mixes by joint dilution with water of the components which are formulated separately, or partly separately.

The herbicidal compositions according to the invention can be formulated in various ways, depending on the prevailing biological and/or physicochemical parameters. Suitable general possibilities for formulations are, for example: wettable powders (WP), emulsifiable concentrates (EC), aqueous solutions (SL), emulsions (EW) such as oil-in-water and water-in-oil emulsions, sprayable solutions or emulsions, oil suspension concentrate (SC), oil- or water-based dispersions, suspoemulsions, dusts (DP), seed dressing products, granules for soil application or for spreading or water-dispersible granules (WG), water-dispersible granules (WDG), water-emulsifiable granules (WEG), ULV formulations, microcapsules or waxes.

The individual types of formulation are known in principle and are described, for example, in: Winnacker-Küchler, "Chemische Technologie" [Chemical Technology], Vol. 7, C. Hauser Verlag Munich, 4th Ed. 1986; van Valkenburg, "Pesticides Formulations", Marcel Dekker N.Y., 1973; K. Martens, "Spray Drying Handbook", 3rd Ed. 1979, G. Goodwin Ltd. London. The formulation auxiliaries required, such as inert materials, surfactants, solvents and other additives, are also known and are described, for example, in: Watkins, "Handbook of Insecticide Dust Diluents and Carriers", 2nd Ed., Darland Books, Caldwell N. J.; H. v. Olphen, "Introduction to Clay Colloid Chemistry"; 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976; Winnacker-Küchler, "Chemische Technologie" [Chemical Technology], Vol. 7, C. Hauser Verlag Munich, 4th Ed. 1986.

Based on these formulations, it is also possible to prepare combinations with other pesticidally active substances, such as other herbicides, fungicides or insecticides, and also safeners, fertilizers and/or growth regulators, for example in the form of a ready mix or tank mix.

Wettable powders are preparations which are uniformly dispersible in water and which, besides the active compound, also comprise ionic or nonionic surfactants (wetting agents, dispersants), for example polyethoxylated alkylphenols, polyethoxylated fatty alcohols or fatty amines, alkanesulfonates or alkylbenzene-sulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or an inert substance.

Emulsifiable concentrates are prepared by dissolving the active compound in an organic solvent, for example butanol, cyclohexanone, dimethylformamide, xylene or else higher-boiling aromatics or hydrocarbons, with the addition of one or more ionic or nonionic surfactants (emulsifiers). Examples of emulsifiers which can be used are: calcium alkylarylsulfonates, such as calcium dodecylbenzenesulfonate, or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

Dusts are obtained by grinding the active compound with finely divided solid materials, for example talc, natural clays, such as kaolin, bentonite and pyrophyllite, or diatomaceous earth.

Granules can be prepared either by spraying the active compound onto adsorptive, granulated inert material, or by applying active compound concentrates to the surface of carriers, such as sand, kaolinite or granulated inert material, with the aid of binders, for example polyvinyl alcohol, sodium polyacrylate or else mineral oils. Suitable active compounds can also be granulated in the manner customary for the preparation of fertilizer granules, if desired as a mixture with fertilizers. Water-dispersible granules are, in general, prepared by processes such as spray-drying, fluidized-bed granulation, disk granulation, mixing using high-speed mixers, and extrusion without solid inert material.

The agrochemical preparations generally comprise from 0.1 to 99 percent by weight, in particular from 0.2 to 95% by weight, of components (A), (B) and (C), the following concentrations being customary, depending on the type of formulation: in wettable powders, the active compound concentration is, for example, approximately 10 to 95% by weight, the remainder to 100% by weight being composed of customary formulation constituents. In the case of emulsifiable concentrates, the active compound concentration can be, for example, from 5 to 80% by weight. Formulations in the form of dusts in most cases comprise from 5 to 20% by weight of active compound, sprayable solutions approximately 0.2 to 25% by weight of active compound. In the case of granules, such as dispersible granules, the active compound content depends partly on whether the active compound is in liquid or solid form and on which granulation auxiliaries and fillers are used. In general, the content in the water-dispersible granules amounts to between 10 and 90% by weight. In addition, the active compound formulations mentioned comprise, if appropriate, the tackifiers, wetting agents, dispersants, emulsifiers, preservatives, antifreeze agents, solvents, fillers, colorants, carriers, antifoams, evaporation inhibitors and pH or viscosity regulators which are customary in each case.

For use, the formulations, which are in commercially available form, are, if appropriate, diluted in a customary manner, for example using water in the case of wettable powders, emulsifiable concentrates, dispersions and water-dispersible granules. Preparations in the form of dusts, soil granules, granules for spreading and sprayable solutions are conventionally not diluted any further with other inert substances prior to use.

The active compounds can be applied to the plants, to parts of plants, to plant seeds or to the area under cultivation (tilled soil), preferably to the green plants and parts of the plants and, if desired, additionally to the tilled soil.

A possible use is the joint application of the active compounds in the form of tank mixes, where the concentrated formulations of the individual active compounds, in the form of their optimal formulations, are mixed jointly with water in the tank, and the spray mixture obtained is applied.

A joint herbicidal formulation of the herbicidal compositions according to the invention has the advantage that it can be applied more easily because the amounts of the components have already been adjusted with respect to one another to the correct ratio. Moreover, the auxiliaries of the formulation can be selected to suit each other in the best possible way, while a tank mix of various formulations may result in undesirable combinations of auxiliaries.

A. FORMULATION EXAMPLES a) A dust (WP) is obtained by mixing 10 parts by weight of an active compound/active compound mixture and 90 parts by weight of talc as inert substance and comminuting the mixture in a hammer mill.

b) A wettable powder (WG) which is readily dispersible in water is obtained by mixing 25 parts by weight of an active compound/active compound mixture, 64 parts by weight of kaolin-containing quartz as inert substance, 10 parts by weight of potassium lignosulfonate and 1 part by weight of sodium oleoylmethyltaurinate as wetting agent and dispersant, and grinding the mixture in a pinned-disk mill.

c) A dispersion concentrate which is readily dispersible in water is obtained by mixing 20 parts by weight of an active compound/active compound mixture with 6 parts by weight of alkylphenol polyglycol ether (Triton X 207), 3 parts by weight of isotridecanol polyglycol ether (8 EO) and 71 parts by weight of paraffinic mineral oil (boiling range for example approximately 255 to 277° (C.) and grinding the mixture in a ball mill to a fineness of below 5 microns.

d) An emulsifiable concentrate (EC) is obtained from 15 parts by weight of an active compound/active compound mixture, 75 parts by weight of cyclohexanone as solvent and 10 parts by weight of ethoxylated nonylphenol as emulsifier.

e) A water-dispersible granule is obtained by mixing
75 parts by weight of an active compound/active compound mixture,
10 parts by weight of calcium lignosulfonate,
5 parts by weight of sodium lauryl sulfate, 3 parts by weight of polyvinyl alcohol and
7 parts by weight of kaolin,
grinding the mixture in a pinned-disk mill and granulating the powder in a fluidized bed by spraying on water as granulation liquid.

f) A water-dispersible granule is also obtained by homogenizing and precomminuting, in a colloid mill, 25 parts by weight of an active compound/active compound mixture, 5 parts by weight of sodium 2,2'-dinaphthylmethane-6,6'-disulfonate, 2 parts by weight of sodium oleoylmethyltaurinate, 1 part by weight of polyvinyl alcohol, 17 parts by weight of calcium carbonate and 50 parts by weight of water, subsequently grinding the mixture in a bead mill and atomizing and drying the resulting suspension in a spray tower by means of a single-substance nozzle.

B. BIOLOGICAL EXAMPLES

1. Herbicidal Post-Emergence Action

Seeds of monocotyledonous and dicotyledonous weed and crop plants are placed into sandy loam in wood fiber pots or in plastic pots, covered with soil and cultivated in a greenhouse, including during the vegetation period outdoors outside of the greenhouse, under good growth conditions. 2-3 weeks after sowing, the test plants are treated at the one- to three-leaf stage. The test compounds, formulated as wettable powders (WP) or liquid (EC) are, in various dosages with a water application rate of 300 I/ha (converted), with added wetting agent (0.2 to 0.3%), sprayed onto the plants and the surface of the soil. 3 to 4 weeks after the treatment of the test plants, the effect of the preparations is rated visually in comparison to untreated controls (herbicidal effect in percent (%): 100% effect=plants have died, 0% effect=like control plants).

Use of Safeners

If it is additionally to be tested as to whether safeners can improve the plant compatibility of test substances in the case of crop plants, the following options are used for applying the safener:

- seeds of the crop plants are, before sowing, dressed with the safener substance (the amount of safener is stated in percent, based on the weight of the seed)
- before the application of the test substances, the crop plants are sprayed with the safener at a certain application rate per hectare (usually 1 day before the application of the test substances)
- the safener is applied together with the test substance as a tank mix (the amount of safener is stated in g/ha or as a ratio, based on the herbicide).

By comparing the effect of the test substances on crop plants without or with safener treatment, it is possible to assess the effect of the safener substance. Here, it is found that the herbicidal activities of the compositions according to the invention exceed the expected values according to Colby which are calculated using the formula below (cf. S. R. Colby; in Weeds 15 (1967) pp. 20-22):

$$E = A + B - \frac{A \times B}{100}$$

Here, the figures denote:

A, B=effect of the component A and B, respectively, in percent

E=expected value in percent

Surprisingly, the compositions according to the invention comprising components (A), (B) and (C) display higher herbicidal activity than compositions comprising components (A) and (B). Likewise surprisingly, the compositions according to the invention comprising components (A), (B) and (C) display better crop plant compatibility than compositions comprising components (A) and (C).

TABLE 1

Post-emergence action

| Component | Dosage [g of a.i./ha] | Activity against STEME | Calculated according to Colby |
|---|---|---|---|
| aminopyralid | 150 | 65% | |
| pyrasulfotole | 12.5 | 60% | |
| aminopyralid + pyrasulfotole | 150 + 12.5 | 95% | 86% |

TABLE 2

Post-emergence action

| Component | Dosage [g of a.i./ha] | Activity against LAMPU | Calculated according to Colby |
|---|---|---|---|
| carfentrazone-ethyl | 25 | 10% | |
| pyrasulfotole | 12.5 | 80% | |
| carfentrazone-ethyl + pyrasulfotole | 25 + 12.5 | 100% | 82% |

TABLE 3

Post-emergence action

| Component | Dosage [g of a.i./ha] | Activity against AVEFA | Calculated according to Colby |
|---|---|---|---|
| imazamox-ammonium | 25 | 60% | |
| pyrasulfotole | 12.5 | 40% | |
| pyroxsulam + pyrasulfotole | 5 + 12.5 | 90% | 76% |

TABLE 4

Post-emergence action

| Component | Dosage [g of a.i./ha] | Activity against VERHE | Calculated according to Colby |
|---|---|---|---|
| pyroxsulam | 5 | 80% | |
| pyrasulfotole | 12.5 | 40% | |
| pyroxsulam + pyrasulfotole | 5 + 12.5 | 90% | 88% |

TABLE 5

Post-emergence action

| Component | Dosage [g of a.i./ha] | Activity against STEME | Calculated according to Colby |
|---|---|---|---|
| aminopyralid | 150 | 65% | |
| pyrasulfotole | 12.5 | 60% | |
| mefenpyr-diethyl | 9.4 | 0% | |
| aminopyralid + pyrasulfotole + mefenpyr-diethyl | 150 + 12.5 + 9.4 | 95% | 86% |

TABLE 6

Post-emergence action

| Component | Dosage [g of a.i./ha] | Activity against MATIN | Calculated according to Colby |
|---|---|---|---|
| mesosulfuron-methyl | 7.5 | 50% | |
| pyrasulfotole | 12.5 | 70% | |
| mefenpyr-diethyl | 9.4 | 0% | |
| mesosulfuron-methyl + pyrasulfotole + mefenpyr-diethyl | 7.5 + 12.5 + 9.4 | 100% | 85% |

TABLE 7

Post-emergence action

| Component | Dosage [g of a.i./ha] | Damage to summer wheat |
|---|---|---|
| mesosulfuron-methyl | 7.5 | 15% |
| pyrasulfotole | 12.5 | 20% |
| mesosulfuron-methyl + pyrasulfotole + mefenpyr-diethyl | 7.5 + 12.5 + 9.4 | 5% |

The invention claimed is:

1. A herbicidal composition, comprising an effective amount of
A) the herbicide pyrasulfotole of the formula (A) or an agriculturally customary salt thereof (component (A)), (A)

[Chemical structure of pyrasulfotole]

B) at least one herbicide (component (B)) selected from the group consisting of aminopyralid, carfentrazone-ethyl, flucarbazone-sodium, florasulam, imazamox-ammonium, iodosulfuron-methyl-sodium, mesosulfuron-methyl, sethoxydim and pyroxsulam, and
C) an amount, acting as an antidote, of at least one safener (component (C)) selected from the group consisting of mefenpyr-diethyl, cloquintocet-mexyl and isoxadifen-ethyl,
wherein said composition comprises the components (A), (B) and (C) in a weight ratio of x:y:z, where x, y and z in each case independently of one another may assume values of from 1 to 200.

2. The herbicidal composition as claimed in claim 1, which comprises the components (A), (B) and (C) in a weight ratio of x:y:z, where x, y and z in each case independently of one another may assume values of from 1 to 100.

3. The herbicidal composition as claimed in claim 1, which comprises the components (A), (B) and (C) in a weight ratio of x:y:z, where x, y and z in each case independently of one another may assume values of from 1 to 50.

4. A method for controlling unwanted vegetation, which comprises applying the herbicidal composition defined according to claim 1 to a plant, to a part of a plant, to a plant seed on to an area on which a plant grows.

5. The herbicidal composition of claim 1, additionally comprising at least one fertilizer.

6. The herbicidal composition of claim 2, additionally comprising at least one fertilizer.

7. The herbicidal composition as claimed in claim 1, in which the herbicide component (B) is imazamox-ammonium, iodosulfuron-methyl-sodium, mesosulfuron-methyl, or sethoxydim.

8. The herbicidal composition as claimed in claim 1, in which the safener component (C) is mefenpyr-diethyl.

9. The herbicidal composition as claimed in claim 1, in which the herbicide component (B) is imazamox-ammonium and the safener component (C) is mefenpyr-diethyl.

10. The herbicidal composition as claimed in claim 1, in which the herbicide component (B) is iodosulfuron-methyl-sodium and the safener component (C) is mefenpyr-diethyl.

11. The herbicidal composition as claimed in claim 1, in which the herbicide component (B) is mesosulfuron-methyl and the safener component (C) is mefenpyr-diethyl.

12. The herbicidal composition as claimed in claim 1, in which the herbicide component (B) is sethoxydim and the safener component (C) is mefenpyr-diethyl.

13. A herbicidal composition according to claim 1, comprising an effective amount of
A) the herbicide pyrasulfotole of the formula (A) or an agriculturally customary salt thereof (component (A)), (A)

[Chemical structure of pyrasulfotole]

B) at least one herbicide (component (B)) selected from the group consisting of aminopyralid, carfentrazone-ethyl, flucarbazone-sodium, florasulam, imazamox-ammonium, iodosulfuron-methyl-sodium, mesosulfuron-methyl, sethoxydim and pyroxsulam, and
C) an amount, acting as an antidote, of at least one safener (component (C)) selected from the group consisting of mefenpyr-diethyl, cloquintocet-mexyl and isoxadifen-ethyl,
wherein said composition comprises the components (A), (B) and (C) in a weight ratio of x:y:z, where x, y and z in each case independently of one another may assume values of from 1 to 200, with the provisos that the ratio of component (A) to component (B) ranges from 1:20 to 20:1 and the ratio of components (A)+(B) to component (C) ranges from 1:5 to 20:1.

14. The herbicidal composition as claimed in claim 13, which comprises the components (A), (B) and (C) in a weight ratio of x:y:z, where x, y and z in each case independently of one another may assume values of from 1 to 50.

15. A method for controlling unwanted vegetation, which comprises applying the herbicidal composition defined according to claim 13 to a plant, to a part of a plant, to a plant seed on to an area on which a plant grows.

16. The herbicidal composition of claim 13, additionally comprising at least one fertilizer.

17. The herbicidal composition as claimed in claim 13, in which the herbicide component (B) is imazamox-ammonium, iodosulfuron-methyl-sodium, mesosulfuron-methyl, or sethoxydim.

18. The herbicidal composition as claimed in claim 13, in which the safener component (C) is mefenpyr-diethyl.

19. The herbicidal composition as claimed in claim 13, in which the herbicide component (B) is imazamox-ammonium and the safener component (C) is mefenpyr-diethyl.

20. The herbicidal composition as claimed in claim 13, in which the herbicide component (B) is iodosulfuron-methyl-sodium and the safener component (C) is mefenpyr-diethyl.

21. The herbicidal composition as claimed in claim 13, in which the herbicide component (B) is mesosulfuron-methyl and the safener component (C) is mefenpyr-diethyl.

22. The herbicidal composition as claimed in claim 13, in which the herbicide component (B) is sethoxydim and the safener component (C) is mefenpyr-diethyl.

* * * * *